(12) United States Patent
Papannagari et al.

(10) Patent No.: US 12,070,253 B2
(45) Date of Patent: Aug. 27, 2024

(54) ORTHOPEDIC IMPLANT WITH IMPROVED VARIABLE ANGLE LOCKING MECHANISM

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Ramprasad Papannagari, Collierville, TN (US); Nicholas S. Ritchey, Collierville, TN (US); Nathaniel Kelley Grusin, Germantown, TN (US); Rick Graber, Cordova, TN (US); Joseph Ferrante, Bartlett, TN (US)

(73) Assignees: Smith & Nephew, Inc.; Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 406 days.

(21) Appl. No.: 17/616,785

(22) PCT Filed: Jun. 2, 2020

(86) PCT No.: PCT/US2020/035729
§ 371 (c)(1),
(2) Date: Dec. 6, 2021

(87) PCT Pub. No.: WO2020/247381
PCT Pub. Date: Dec. 10, 2020

(65) Prior Publication Data
US 2022/0233222 A1 Jul. 28, 2022

Related U.S. Application Data
(60) Provisional application No. 62/858,727, filed on Jun. 7, 2019.

(51) Int. Cl.
*A61B 17/80* (2006.01)
*A61B 17/70* (2006.01)

(52) U.S. Cl.
CPC ...... *A61B 17/8047* (2013.01); *A61B 17/7059* (2013.01); *A61B 17/8014* (2013.01); *A61B 17/8052* (2013.01)

(58) Field of Classification Search
CPC ................................................. A61B 17/8052
See application file for complete search history.

(56) References Cited

U.S. PATENT DOCUMENTS 7,637,928 B2 12/2009 Fernandez
8,343,196 B2 1/2013 Schneider
(Continued)

FOREIGN PATENT DOCUMENTS

CN 101772329 A 7/2010
DE 102005015496 B4 11/2006
(Continued)

OTHER PUBLICATIONS

International Search Report and Written Opinion for International application No. PCT/US2020/035729, mailed on Oct. 16, 2020, 13 pages.
(Continued)

*Primary Examiner* — David W Bates
(74) *Attorney, Agent, or Firm* — KDW Firm PLLC

(57) ABSTRACT

An orthopedic implant including an outer surface and at least one opening extending through the outer surface for receiving a fastener for coupling the implant to a patients bone or bone portion/fragment. The opening including a plurality of fins circumferentially disposed about the opening for engaging threads formed on a head portion of the fastener to secure the fastener to the implant. The plurality of fins being arranged and configured in first and second (Continued)

vertically spaced rows of fins. At least one of the fins including a different configuration, property, etc. relative to at least one of the other plurality of fins. In one embodiment, each of the first and second fins in a vertically stacked relationship includes a different configuration from the other of the first and second fins in that stack. In one embodiment, the different configuration includes a different length, a different thickness, or a combination thereof.

10 Claims, 7 Drawing Sheets

(56) References Cited

U.S. PATENT DOCUMENTS

| | | | |
|---|---|---|---|
| 8,574,268 B2* | 11/2013 | Chan | B23G 1/02 |
| | | | 606/280 |
| 8,870,931 B2 | 10/2014 | Dahners et al. | |
| 8,940,029 B2* | 1/2015 | Leung | A61B 17/8605 |
| | | | 606/291 |
| 10,335,212 B2* | 7/2019 | Paolino | A61B 17/8605 |
| 10,772,665 B2* | 9/2020 | Bosshard | A61B 17/8052 |
| 10,925,651 B2* | 2/2021 | Rush | A61B 17/1728 |
| 11,013,541 B2* | 5/2021 | Bosshard | A61B 17/8057 |
| 11,179,180 B2* | 11/2021 | Oberli | A61L 31/022 |
| 2003/0225409 A1 | 12/2003 | Freid et al. | |
| 2004/0073218 A1* | 4/2004 | Dahners | A61B 17/8057 |
| | | | 606/291 |
| 2005/0165400 A1* | 7/2005 | Fernandez | A61B 17/8057 |
| | | | 606/291 |
| 2008/0234677 A1* | 9/2008 | Dahners | A61B 17/8057 |
| | | | 606/60 |
| 2008/0234749 A1* | 9/2008 | Forstein | A61B 17/8057 |
| | | | 606/291 |
| 2011/0238122 A1* | 9/2011 | Gradl | A61B 17/8052 |
| | | | 606/289 |
| 2012/0143193 A1 | 6/2012 | Hulliger | |
| 2012/0323284 A1* | 12/2012 | Baker | A61B 17/8052 |
| | | | 606/280 |
| 2014/0277180 A1 | 9/2014 | Paolino et al. | |
| 2016/0089191 A1* | 3/2016 | Pak | A61B 17/8047 |
| | | | 606/291 |
| 2018/0000528 A1 | 1/2018 | Austin et al. | |
| 2018/0064479 A1* | 3/2018 | Lopez | A61B 17/8061 |
| 2018/0250043 A1* | 9/2018 | Rapalo | A61B 17/8052 |
| 2021/0145493 A1* | 5/2021 | Kodvanj | A61B 17/8057 |

FOREIGN PATENT DOCUMENTS

| | | |
|---|---|---|
| DE | 102005042766 B4 | 1/2007 |
| WO | 2013059090 A1 | 4/2013 |

OTHER PUBLICATIONS

Ortholoc®3Di Foot Reconstruction System—Surgical Technique, Wright, Mar. 14, 2016, 28 pages.
China Patent Office, First Office Action with Translation, dated Feb. 29, 2024, 12 pages.

* cited by examiner

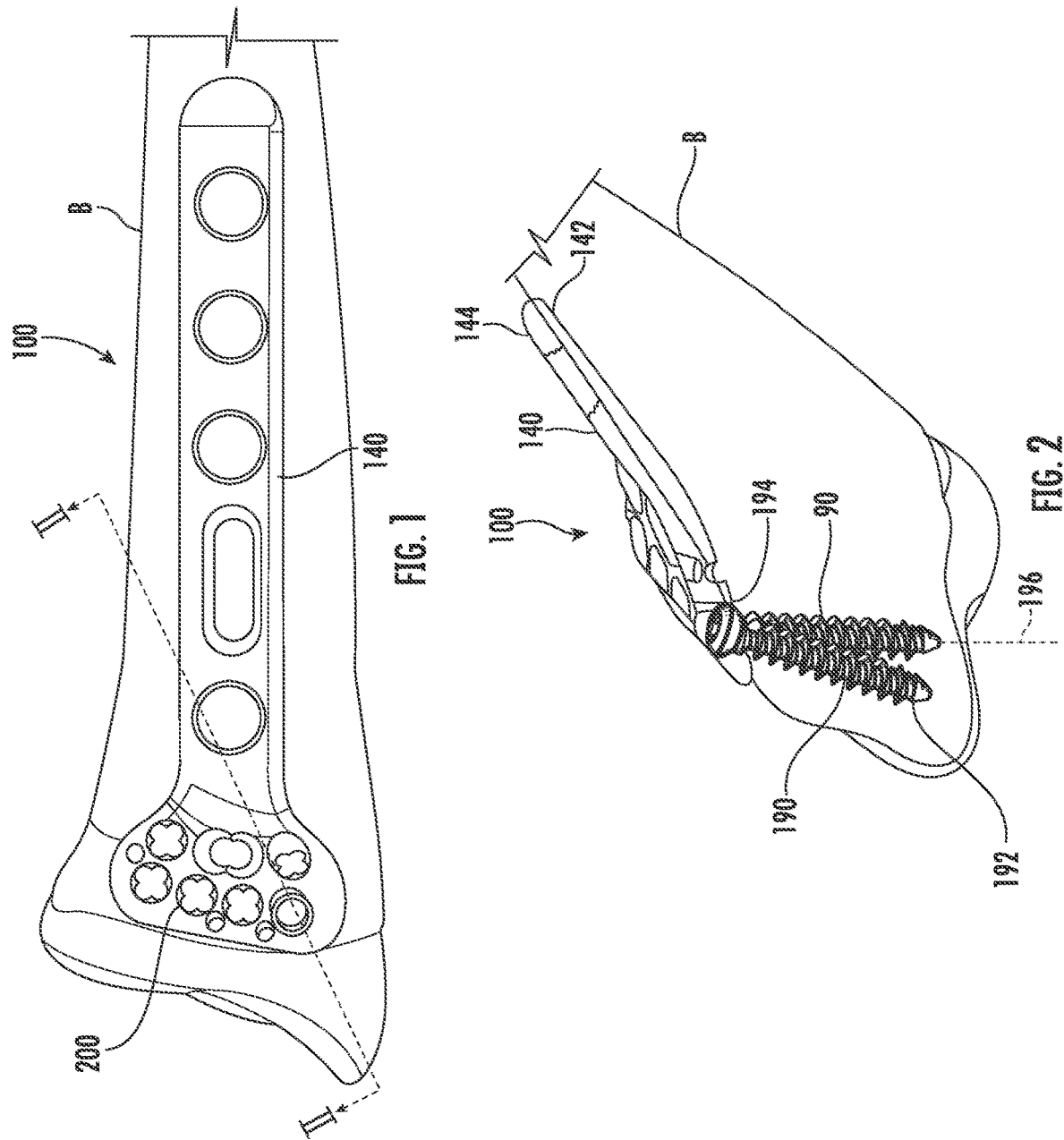

ORTHOPEDIC IMPLANT WITH IMPROVED VARIABLE ANGLE LOCKING MECHANISM

CROSS-REFERENCE TO RELATED APPLICATION

This application is a National Phase filing of International Application No. PCT/US2020/035729, filed Jun. 2, 2020, which claims the benefit of U.S. Provisional Patent Application No. 62/858,727, filed Jun. 7, 2019, entitled "Orthopedic Implant with Improved Variable Angle Locking Mechanism," the entire contents of each application is hereby incorporated by reference in its entirety.

TECHNICAL FIELD

The present disclosure is directed to orthopedic implants for coupling to one or more patient's bones, bone portions, bone fragments, etc., and more specifically to orthopedic implants having improved variable angle locking mechanisms for enabling polyaxial placement and fixation of a fastener.

BACKGROUND

Bone fractures are often repaired by securing an orthopedic implant to one or more patient's bone(s), bone portions, bone fragments, etc. (used interchangeably without the intent to limit). For example, in one procedure, a bone plate is coupled to a patient's bone across the fracture. Generally speaking, in use, a bone plate is positioned so that portions thereof are placed on either side of the fracture and fasteners (e.g., screws) are placed through openings formed in each bone plate portion. Depending upon which bone is to be treated, the bone plate may be straight or curved to match the contour of the bone for which it is designed. Bone plates may also be provided in many shapes and sizes. In use, the bone plate promotes healing of the fracture by providing a rigid fixation or support structure between the bone and the plate.

Bone plates may be secured to the bone in a number of ways. An existing solution is a plate and screw system where the fasteners, screws, etc. (used interchangeably herein without the intent to limit) are locked to the plate. A bone screw is threaded through an opening in the plate and into the bone. The screw is then secured to the bone plate via threads formed on the head portion of the bone screw that cooperate with the threaded opening formed in the bone plate. This secures the plate with respect to the bone and provides rigid fixation between the bone plate and screw(s). That is, because the head portion of the bone screw interdigitates with the threads formed in the bone plate, the plate and screws(s) form a stable system or construct, and the stability of the fracture can be dependent on or aided by the stiffness of the construct. Locking a screw into the plate can achieve angular and axial stability and eliminate the possibility for the screw to toggle, slide, or be dislodged, reducing the risk of postoperative loss of reduction.

However, although locking screws may reduce the incidence of loosening, they provide a limited range of fixation between the plate and the screw(s). That is, because of the interlocking screw threads between the head portion of the bone screw and the threaded opening formed in the bone plate, the insertion angle of the bone screw through the bone plate is limited. Generally speaking, the longitudinal axis of the bone screw lines up with a central axis of the opening, and no, or limited, angular variation is allowed. Thus, limiting use of locking screws in some instances.

For example, when treating a severe fracture, bone fragments may be shattered and located in irregular positions. Although a surgeon may wish to obtain the benefits of a locking screw and bone plate used together, the angle at which the locking screw extends from the plate at a certain opening may not be the angle that would allow the surgeon to grab, seize, fix, or otherwise secure, the desired, random bone fragment. In this case, the surgeon may need to secure the plate to the bone somewhere else, or use a non-locking screw. Although non-locking screws do not lock into the plate, they can be inserted at various angles.

Specifically, non-locking screws are secured into bone in the same way that locking screws are, but they are not secured to the plate. That is, non-locking screws typically include rounded and/or smooth head portions. Thus, one advantage of non-locking screws is that they can be inserted at various angles because they are not limited by the thread-to-thread connection of locking screws with the bone plate. However, if the surgeon desires the rigid stable construct of a locking screw and plate, the use of a non-locking screw to obtain the desired angular orientation is not necessarily optimal.

There have been bone plating systems developed that provide the surgeon with the option of choosing a non-locking screw or a locking screw. For example, systems have been developed where the bone plate includes threaded holes for receiving locking screws or non-locking screws, and non-threaded holes for receiving non-locking screws. Also, systems have been developed where the bone plate includes partially threaded slots to allow either non-locking or locking screws to be used together. Such combination slots provide surgeons with the intraoperative choice about whether to use the plate with locking screws, non-locking screws, or with a combination of both. However, these systems have inherent disadvantages. For example, the combination slots may not be able to maintain the fixed angular relationship between the screw(s) and plate under physiological loads.

There have been other attempts to provide increased polyaxial locking systems that provide increased range of angular displacement. For example, U.S. Pat. No. 8,105,367, issued on Jan. 31, 2012, entitled Bone Plate and Bone Plate Assemblies including Polyaxial Fasteners, incorporated herein by reference in its entirety. In particular, U.S. Pat. No. 8,105,367 describes an implant having fastener receiving openings with a single layer of fins that project into the opening. In use, the fins permit a fastener to be positioned off-axis within the opening.

While currently-available implants have produced excellent results, many of these implants exhibit one or more shortcomings or disadvantages. For example, it would be beneficial to provide orthopedic implants such as, for example, bone plates, that provide for increased angular displacement of the fasteners with respect to the implant while maintaining secure engagement between the fasteners and the implant. It is with this in mind that the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is an orthopedic implant such as, for example, a bone plate. In one embodiment, the implant includes at least one opening formed therein for receiving a fastener such as, for example, a bone screw. The at least one opening including a plurality of fins, tabs, projections, etc. (used interchangeably herein without the intent to limit). The plurality of fins being arranged in first and second layers, rows, etc. (used interchangeably herein without the intent to limit). Each row including a plurality of fins such as, for example, four fins orientated ninety-degrees apart from each other. In one embodiment, at least one of the fins has a different configuration from at least one of the other remaining fins.

In one embodiment, each of the first or upper fins and the second or lower fins in the first and second rows may be arranged and configured in a vertically stacked relationship so that the second/lower fin is aligned with, positioned beneath, etc. the first/upper fin in a vertical stack.

In one embodiment, for each of the vertical stacks of first/upper and second/lower fins, the first/upper fin may have a different configuration as compared to the second/lower fin in its vertical stack.

In one embodiment, each of the first/upper fins and second/lower fins may alternate configurations as the fins are circumferentially disposed in the at least one opening. For example, with the at least one opening including four first/upper fins and four second/lower fins orientated in a vertically stacked relationship so that, for example, first/upper and second/lower fins are located at 12 O'clock, 3 O'clock, 6 O'clock, and 9 O'clock, the first/upper fin at 12 O'clock and 6 O'clock may have a different configuration as compared to the second/lower fin at 12 O'clock and 6 O'clock (e.g., the first/upper fins may have a first configuration and the second/lower fins may have a second configuration). Similarly, the first/upper fins located at 3 O'clock and 9 O'clock may have a different configuration as compared to the second/lower fin at 3 O'clock and 9 O'clock (e.g., the first/upper fins may have the second configuration and the second/lower fins may have the first configuration). Thus arranged, as one moves about the circumference of the at least one opening, the first/upper fin at each clock position may have a different configuration from the second/lower fin at the same clock position, with the first/upper and second/lower fins alternating configurations as one traverses about the circumference of the opening.

In one embodiment, the different configurations may correspond to a different length (e.g., as measured from a base of the fin to a terminal end of the fin), or a different thickness (e.g., cross-sectional diameter, thickness, etc.), or a combination thereof. Thus arranged, for example, as one moves about the circumference of the at least one opening, the first/upper fin at a first clock position may have a longer length and/or thinner cross-section than the second/lower fin at the first clock position. Thereafter, at a subsequent clock position, the second/lower fin at a second clock position may have a longer length and/or thinner cross-section than the first/upper fin at the second clock position, and so on as one traverses about the circumference of the opening.

In one embodiment, the orthopedic implant may be a bone plate. The bone plate including at least one opening including first and second rows of fins. In one embodiment, each of the first and second rows of fins may include four fins orientated ninety-degrees apart. The first and second fins being orientated in a vertically stacked relationship. In one embodiment, the first fin in a stacked relationship may extend into the opening farther than the second fin in the stacked relationship (e.g., the first fin may have a longer length as measured from its base to its tip than the second fin). Alternatively, and/or in addition, the first fin in the stacked relationship may be thinner (e.g., have a smaller cross-sectional area) than the second fin in the stacked relationship.

In addition, and/or alternatively, adjacent sets of first and second vertically stacked fins may alternate configurations so that, at the next adjacent position, the first fin may be shorter than the second fin. Alternatively, and/or in addition, the first fin may be thicker than the second fin, and so on as one traverses about the circumference of the opening.

In one embodiment, an orthopedic implant is disclosed. The orthopedic implant include an outer surface and at least one opening extending through the outer surface and including a plurality of first fins and a plurality of second fins circumferentially disposed about the at least one opening. The plurality of first fins are positioned in a vertically stacked relationship relative to the plurality of second fins. The plurality of first fins and the plurality of second fins are adapted and configured to deflect or deform in order to secure a position of a head of a bone fastener inserted into the at least one opening. In one embodiment, at least one of the plurality of fins includes a different configuration from at least one of the other plurality of fins.

In one embodiment, the at least one of the plurality of fins includes a first configuration and the at least one of the other plurality of fins includes a second configuration, the first configuration being different from the second configuration.

In one embodiment, the different configurations is selected from one of a different size or length, or a different thickness (e.g., cross-sectional area), or a combination thereof.

In one embodiment, the plurality of first and second fins orientated in a vertically stacked relationship are arranged and configured so that a first fin in a first vertically stacked position includes a different configuration from a second fin in the first vertically stacked position.

In one embodiment, the plurality of first and second fins each include four fins orientated ninety-degrees apart so that the first and second fins are vertically stacked at position A, position B, position C, and position D. The first fins at positions A, B, C, and D each having a different configuration than the second fin at positions A, B, C, and D, respectively.

In one embodiment, the first fins at positions A and C each include a first configuration, the second fins at positions A and C each include a second configuration different from the first configuration. In one embodiment, the second fins at positions B and D include the first configuration and the first fins at positions B and D include the second configuration.

In one embodiment, an orthopedic implant is disclosed. The orthopedic implant includes a bone contacting surface, an upper surface opposite the bone contacting surface, and a plurality of openings extending between the bone contacting surface and the upper surface, each of the plurality of openings being arranged and configured to receive a fastener for coupling the orthopedic implant to a patient's bone in use. At least one of the plurality of openings including first and second rows of fins. Each of the first and second rows of fins including a plurality of fins circumferentially disposed about the at least one opening, the plurality of fins being arranged and configured to engage a head portion of a respective fastener inserted therein. At least one of the plurality of fins in the first and second rows of fins has a different configuration from at least one of another one of the plurality of fins in the first and second rows of fins.

In one embodiment, each of the plurality of fins in the first row of fins is arranged and configured in a vertically stacked relationship with one of the plurality of fins in the second row of fins so that the second row of fins is circumferentially aligned with the first row of fins.

In one embodiment, for each of the vertical stacks of first and second rows of fins, the fin in the first row of fins has a different configuration as compared to the fin in the second row of fins in its respective vertical stack.

In one embodiment, each fin in the first and second rows of fins includes an alternating configuration of fins as the fins are circumferentially disposed in the at least one opening.

In one embodiment, each of the first and second rows of fins include four fins orientated ninety-degrees apart so that the four fins in the first and second rows of fins are positioned in circumferential positions A, B, C, and D. The fin in the first row of fins at positions A and C includes a first configuration, the fin in the first row of fins at positions B and D includes a second configuration, the fin in the second row of fins at positions A and C includes the second configuration, and the fin in the second row of fins at positions B and D includes the first configuration.

In one embodiment, as one moves about a circumference of the at least one opening, each fin in the first row of fins has a different configuration as compared to each fin in the second row of fins in its respective vertical stack, with each fin in the first row of fins and each fin in the second row of fins alternating configurations.

In one embodiment, the different configuration of fins is selected from one of a different length, a different thickness, or a combination thereof.

In one embodiment, at least one of the fins in the first row of fins extends into the at least one opening farther than the fin in the second row of fins in the vertically stacked relationship.

In one embodiment, at least one of the fins in the first row of fins has a thinner cross-sectional area at a tip thereof as compared to the fin in the second row of fins in the vertically stacked relationship.

In one embodiment, the orthopedic implant is a bone plate.

In one embodiment, a bone plate is disclosed. The bone plate includes a top surface, a bone contacting surface, and at least one opening extending between the top surface and the bone contacting surface, the at least one opening including first and second rows of fins, each of the first and second rows of fins including a plurality of fins circumferentially disposed about the at least one opening, the fins in the first row of fins being aligned in a vertically stacked relationship with the fins in the second row of fins. For each vertically stacked relationship, the fin in the first row of fins has one of a first configuration and a second configuration, the fin in the second row of fins has the other one of the first configuration and the second configuration, the first configuration being different than the second configuration.

In one embodiment, the first configuration is a different length as measured from a base of the fin to a tip of the fin, the second configuration is a thinner cross-sectional area at the tip of the fin.

In one embodiment, the fins in the first row of fins alternate first and second configurations as one moves about a circumference of the at least one opening; and the fins in the second row of fins alternate first and second configurations as one moves about the circumference of the at least one opening.

In one embodiment, the first configuration is a different length as measured from a base of the fin to a tip of the fin, the fins in the first and second row of fins alternating first and second configurations as one moves about a circumference of the at least one opening so that a longer length fin alternates between the first and second rows of fins as one moves about the circumference of the at least one opening.

In one embodiment, each of the first and second rows of fins include four fins orientated ninety-degrees apart so that the four fins in the first and second rows of fins are positioned in circumferential positions A, B, C, and D. The fin in the first row of fins at positions A and C includes the first configuration, the fin in the first row of fins at positions B and D includes the second configuration, the fin in the second row of fins at positions A and C includes the second configuration, and the fin in the second row of fins at positions B and D includes the first configuration.

In one embodiment, the orthopedic implant further includes at least one fastener for receipt within the at least one opening. The fastener being at least partially threaded and having a head portion and a shaft portion. The plurality of first and second fins are deflectable, deformable, or a combination thereof, relative to the head portion of the fastener so that when the fastener is inserted into the opening, the fastener is retained at any one of a plurality of angles relative to the opening. In use, the plurality of first and second fins are deformable, deflectable, or a combination thereof, so that at least some of the first and second fins are interposed between adjacent threads formed on the head portion of the fastener.

In one embodiment, an orthopedic implant including an outer surface and at least one opening extending through the outer surface for receiving a fastener for coupling the implant to a patient's bone or bone portion/fragment is disclosed. The opening including a plurality of fins circumferentially disposed about the opening for engaging threads formed on a head portion of the fastener to secure the fastener to the implant. The plurality of fins being arranged and configured in first and second vertically spaced rows of fins. At least one of the fins including a different configuration, property, etc. relative to at least one of the other plurality of fins. In one embodiment, each of the first and second fins in a vertically stacked relationship includes a different configuration from the other of the first and second fins in that stack. In one embodiment, the different configuration includes a different length, a different thickness, or a combination thereof.

Embodiments of the present disclosure provide numerous advantages. For example, use of the coupling mechanism of the present disclosure enables a surgeon to polyaxially position the fastener relative to the implant to provide increased versatility while providing a better coupling between the fastener and the implant to avoid, or at least minimize, the risk of the fastener dislodging from the implant after implantation.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which:

FIG. 1 is an illustration of an example embodiment of an orthopedic implant (shown as a bone plate positioned on a bone);

FIG. 2 is a cross-sectional view of the orthopedic implant taken along line II-II of FIG. 1;

Figure 3:
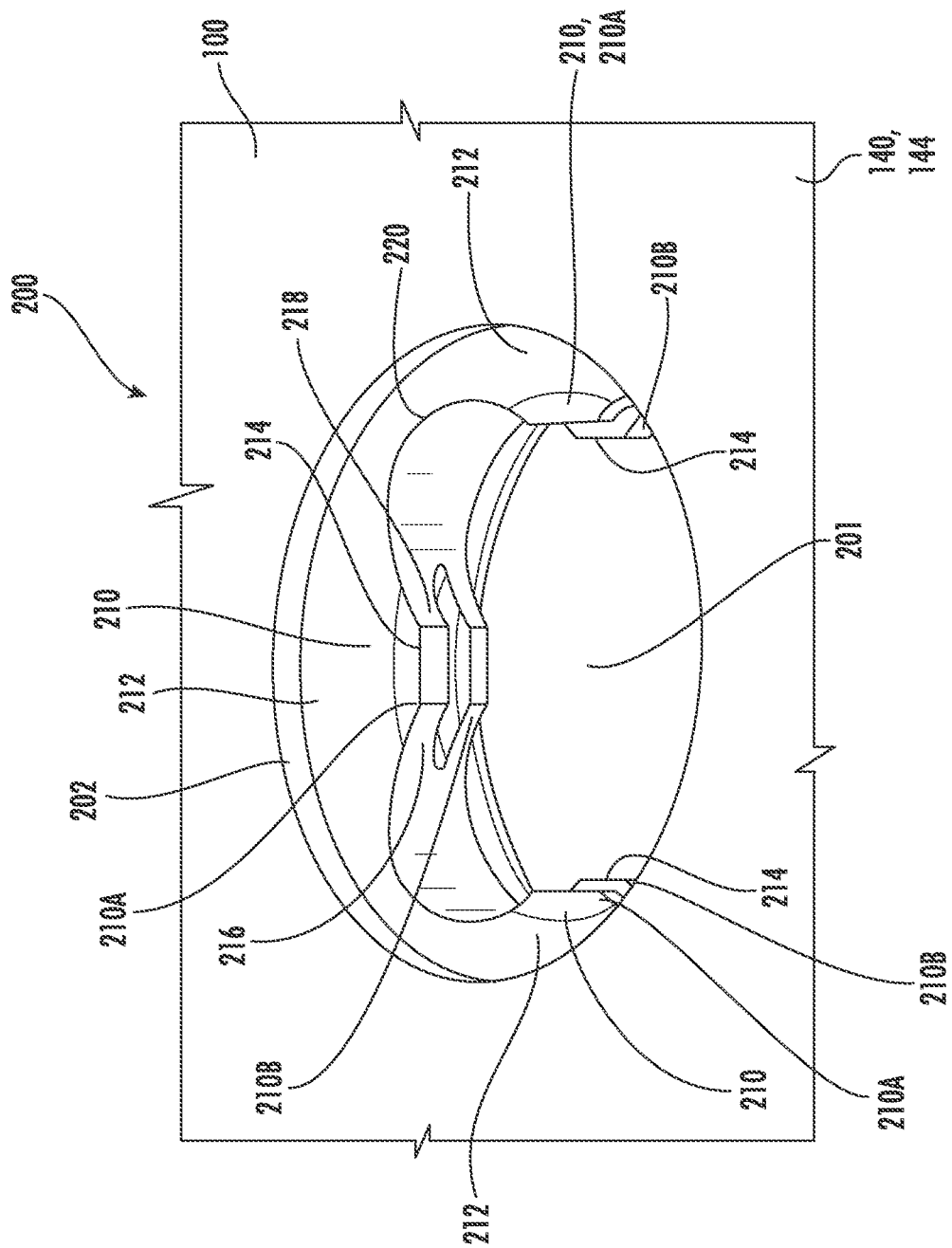
FIG. 3 is a perspective view of a variable angle locking mechanism for receiving a fastener that may be used in connection with the orthopedic implant shown in FIG. 1.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein.

DETAILED DESCRIPTION

Various features, aspects, or the like of an orthopedic implant or device (used interchangeably herein without the intent to limit) will now be described more fully hereinafter with reference to the accompanying drawings, in which one or more aspects or features of the orthopedic implant will be shown and described. It should be appreciated that the various features, aspects, or the like may be used independently of, or in combination, with each other. It will be appreciated that an orthopedic implant as disclosed herein may be embodied in many different forms and should not be construed as being limited to the embodiments set forth herein. Rather, these embodiments are provided so that this disclosure will convey certain aspects or features of the orthopedic implant to those skilled in the art. In the drawings, like numbers refer to like elements throughout unless otherwise noted.

Disclosed herein is an orthopedic implant including an improved variable angled coupling, securing, locking, etc. (used interchangeably herein without the intent to limit) mechanism for enabling increased polyaxial angular rotation of fasteners relative to the implant. As will be illustrated and described, in one embodiment, the orthopedic implant may be in the form of a bone plate. However, as will be appreciated by one of ordinary skill in the art, the orthopedic implant may be any now known or hereafter developed implant that receives a fastener for coupling to a patient's bone, bone portions, bone fragments, etc. (used interchangeably herein without the intent to limit) including, for example, an intramedullary nail, a knee replacement device, a hip replacement device, an acetabular cup, an acetabular cage, an external fixation device, etc.

Moreover, the orthopedic implant may have any shape and/or configuration, which, as will be appreciated by one of ordinary skill in the art, may be dependent on the location and type of patient's bone being fixed. For example, a bone plate may include a bone conforming arcuate surface. In addition, the bone plate may be arranged and configured to contact a distal femur, a proximal femur, a distal tibia, a proximal tibia, a proximal humerus, a distal humerus, a clavicle, a fibula, an ulna, a radius, a distal radius, a rib, pelvis, a vertebra, bones of the foot, or bones of the hand, shaft fractures on long bones, or any of the aforementioned adjacent bones in the case of a joint fusion plate.

In addition, the implant such as, for example, the bone plate, may include any now known or hereafter developed additional features such as, for example, one or more openings or slots designed to receive, for example, surgical implantation tools, different fasteners (e.g., non-locking fasteners), k-wires, or the like.

The orthopedic implant may be manufactured from any suitable material now known or hereafter developed, including, for example, metals, polymers, plastics, ceramics, resorbable, non-resorbable, composite materials, etc. Suitable materials may include, for example, titanium, stainless steel, cobalt chrome, polyetheretherketone (PEEK), polyethylene, ultra-high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a patient's body. In some embodiments, the fastener may be manufactured from the same material as the implant. In other embodiments, the fasteners may be manufactured from a different material as compared to the implant.

The fastener can be any type of fastener now known or hereafter developed. For example, the fastener may include any type of external thread including standard or non-standard threads. For example, the external threads can be arranged as a continuous ridge or a non-continuous ridge. The external threads can form a portion of a revolution, one complete revolution, multiple revolutions, a single lead, multiple leads, or any other threads known in the art. Additionally, and/or alternatively, in the case of locking screws, the head portion of the fastener can include any surface that will engage with and seat within the opening. For example, the head portion can include threads (as will be described herein). Alternatively, the head portion can include a series of dimples, ridges, bumps, textured areas, or any other surface that can secure the fastener.

The fastener may be any typical fastener, made out of any appropriate material. The fastener may include a bore for receiving a driver in order to drive the fastener through the implant and into the patient's bone. The bore may be any size and shape, for example, it may have a hexagonal configuration to receive a corresponding hexagonal driver, a Phillips screw head, a flat-head, a star configuration, Torx, or any other appropriate configuration that can cooperate with a driver to drive the fastener through the implant and into the patient's bone.

The shaft of the fastener may be fully threaded, partially threaded, or a helical blade, and/or may include one or more tacks, deployable talons, expandable elements, or any feature that allows the shaft to engage the patient's bone. It is also possible that shaft be non-threaded so that the fastener takes the form of a peg or a pin. This alternative implementation may be preferred in certain procedures where, for instance, the main goal is to prevent tilting of a bone segment or in procedures where there is no concern of the fastener pulling out from the patient's bone and hence no need for the shaft to be threaded or otherwise configured to engage the patient's bone. The end of the shaft may be a self-tapping or self-drilling tip.

In any event, as will be readily apparent from the remaining disclosure, the focus of the present disclosure is on example embodiments of finned openings formed in the orthopedic implant for receiving a fastener. Thus, it should be appreciated that the present disclosure should not be limited to any particular type of orthopedic implant having any particular configuration unless specifically claimed.

Referring to FIGS. 1 and 2, an orthopedic implant 100 may be a bone plate for repairing fractures in a patient's bone or bone portions B. That is, as shown, the orthopedic implant 100 may be in the form of a bone plate 140 including one or more fasteners 190 for securing the implant (e.g., bone plate) 140 to the patient's bone B. As previously mentioned, the orthopedic implant 100 may be any now known or hereafter developed implant receiving a fastener for securing to a patient's bone or bone portions B. Similarly, the fastener 190 may be any now known or hereafter developed fastener. As shown, in one embodiment, the fastener 190 includes a head portion 194 and a shaft portion 192. The shaft portion 192 may be threaded or non-threaded. The head portion 194 of the fastener 190 includes at least one thread or the like. The head portion 194 may include a bore for receiving a driver in order to drive the fastener 190 through the plate 140 and into the patient's bone B.

As shown, the bone plate 140 may include one or more openings 200 for receiving a head portion 194 of a fastener 190 inserted therein. That is, as will be appreciated by one of ordinary skill in the art, the bone plate 140 may include a lower or bone contacting surface 142, an upper surface 144 opposite the lower or bone contacting surface 142, and a plurality of openings 200 extending between the upper surface 144 and the lower or bone contacting surface 142 for receiving a plurality of fasteners 190, respectively, for coupling the bone plate 140 to the patient's bone or bone portions B. As will be described herein, one or more of the openings 200 include a plurality of fins for coupling with, engaging, etc. the head portion 194 of the fastener 190 inserted therein (referred to herein as a finned opening). In use, the finned openings 200 can be positioned anywhere on the implant (e.g., bone plate) 100. In use, the fastener 190 can be inserted into the finned opening 200 and fixed relative to the plate 140 at various insertion angles to capture random bone portions, fragments, etc. that have split from the bone during fracture and secure the bone portions, fragments, etc. to the plate 140.

As schematically shown in FIG. 2, the finned openings 200 enable a fastener 190 inserted therein to achieve a greater range of insertion angles as compared to, for example, a conventional locking screw 90 that is threadably coupled to the bone plate 140. For example, in one embodiment, the angular position of the fastener 190 may be rotated through a range of approximately ±15 degrees, although the range of allowable polyaxial rotation can vary, including greater and less than the fifteen degrees.

Figure 4:
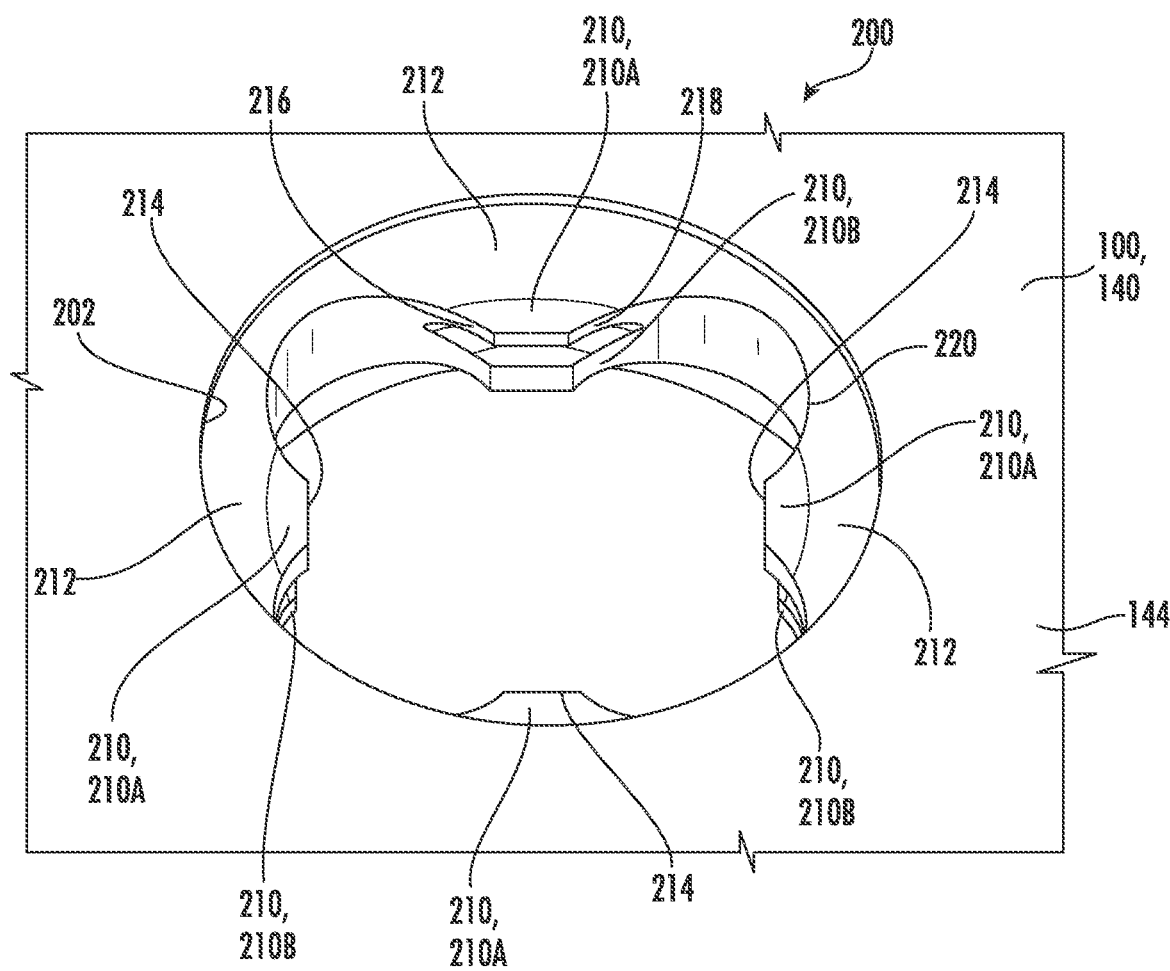
FIG. 4 is an alternate perspective view of the variable angle locking mechanism shown in FIG. 3.
Figure 5:
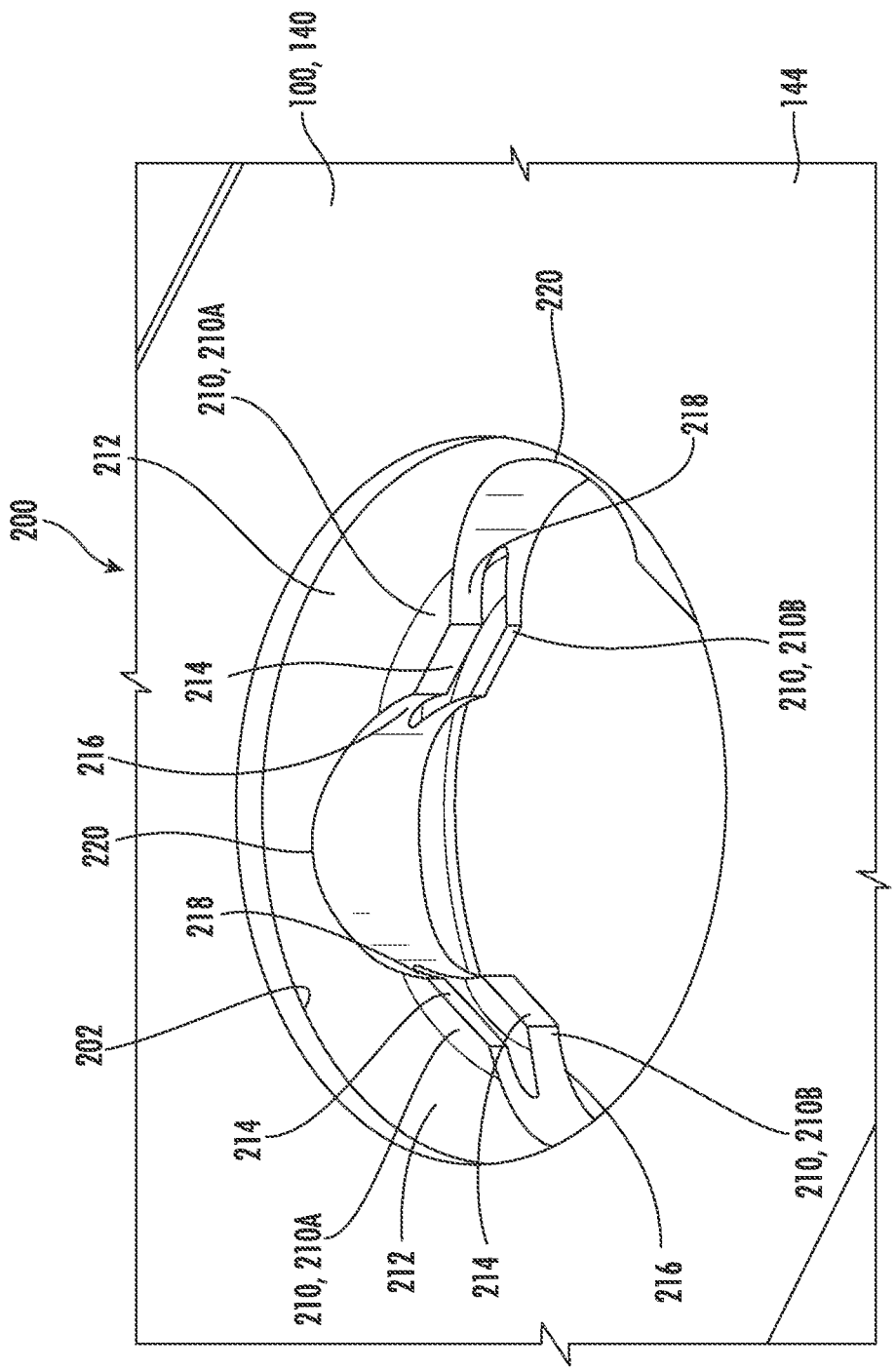
FIG. 5 is an alternate perspective view of the variable angle locking mechanism shown in FIG. 3.
Figure 6:
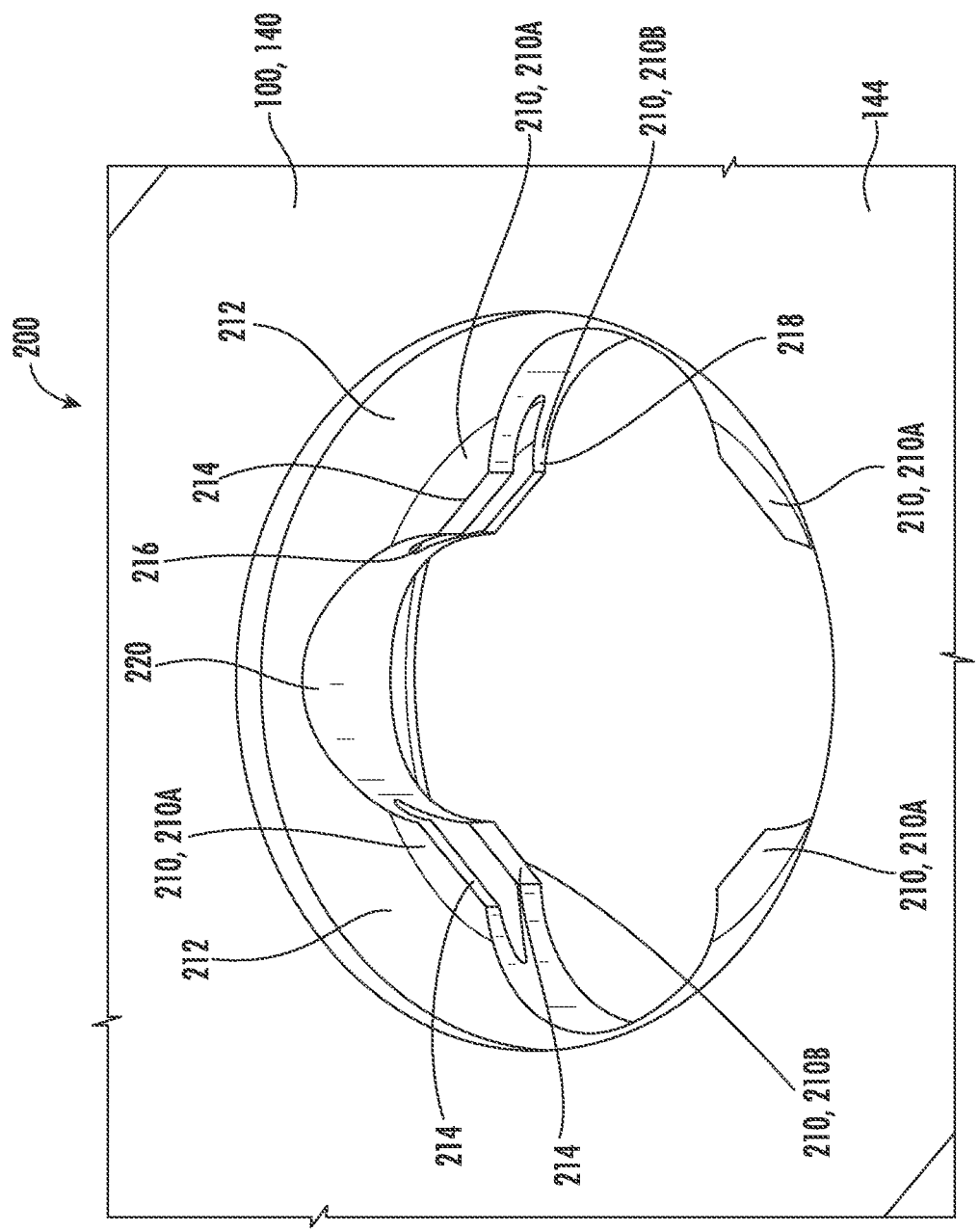
FIG. 6 is an alternate perspective view of the variable angle locking mechanism shown in FIG. 3.
Figure 7:
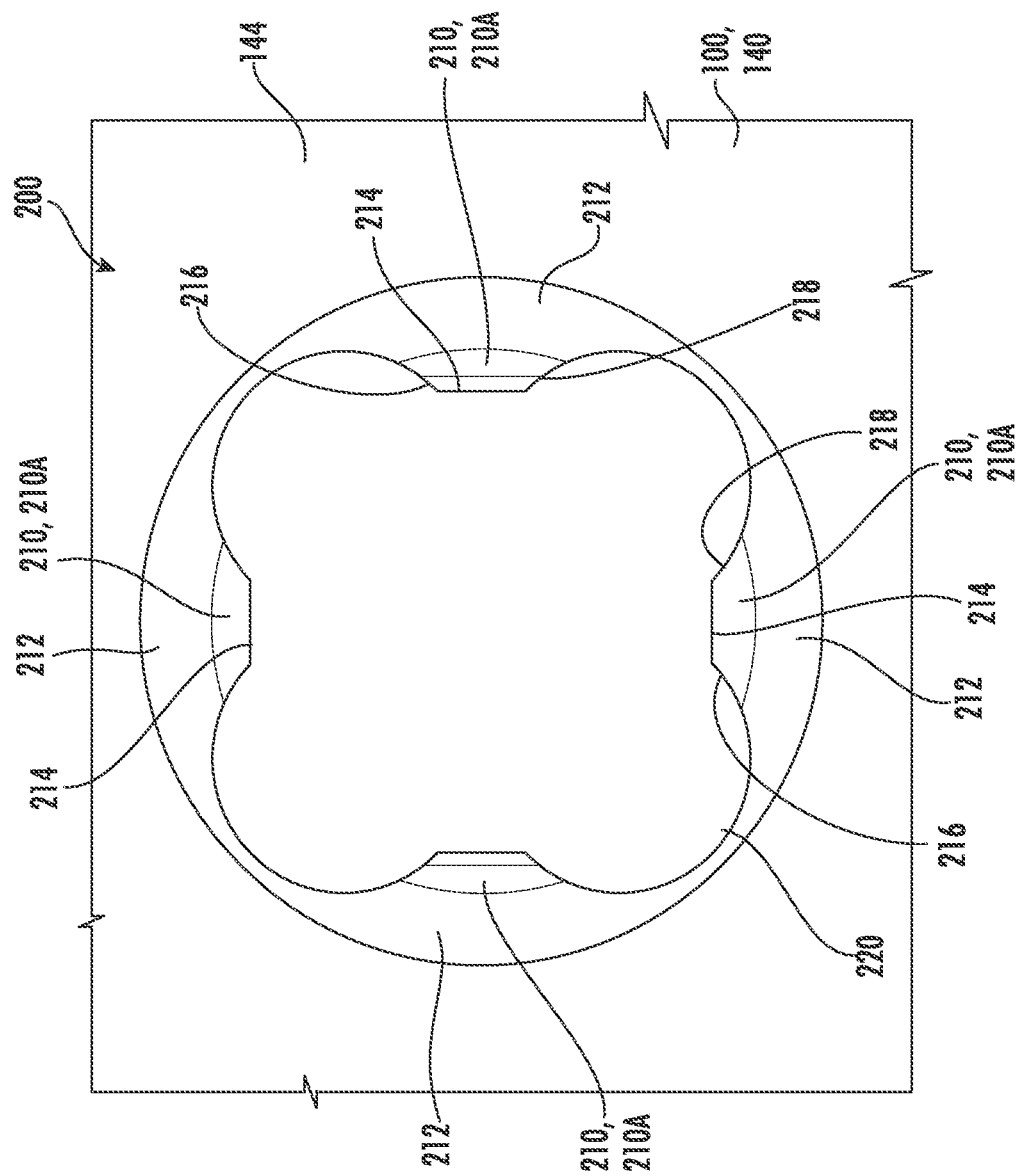
FIG. 7 is a top view of the variable angle locking mechanism shown in FIG. 3.
Figure 8:
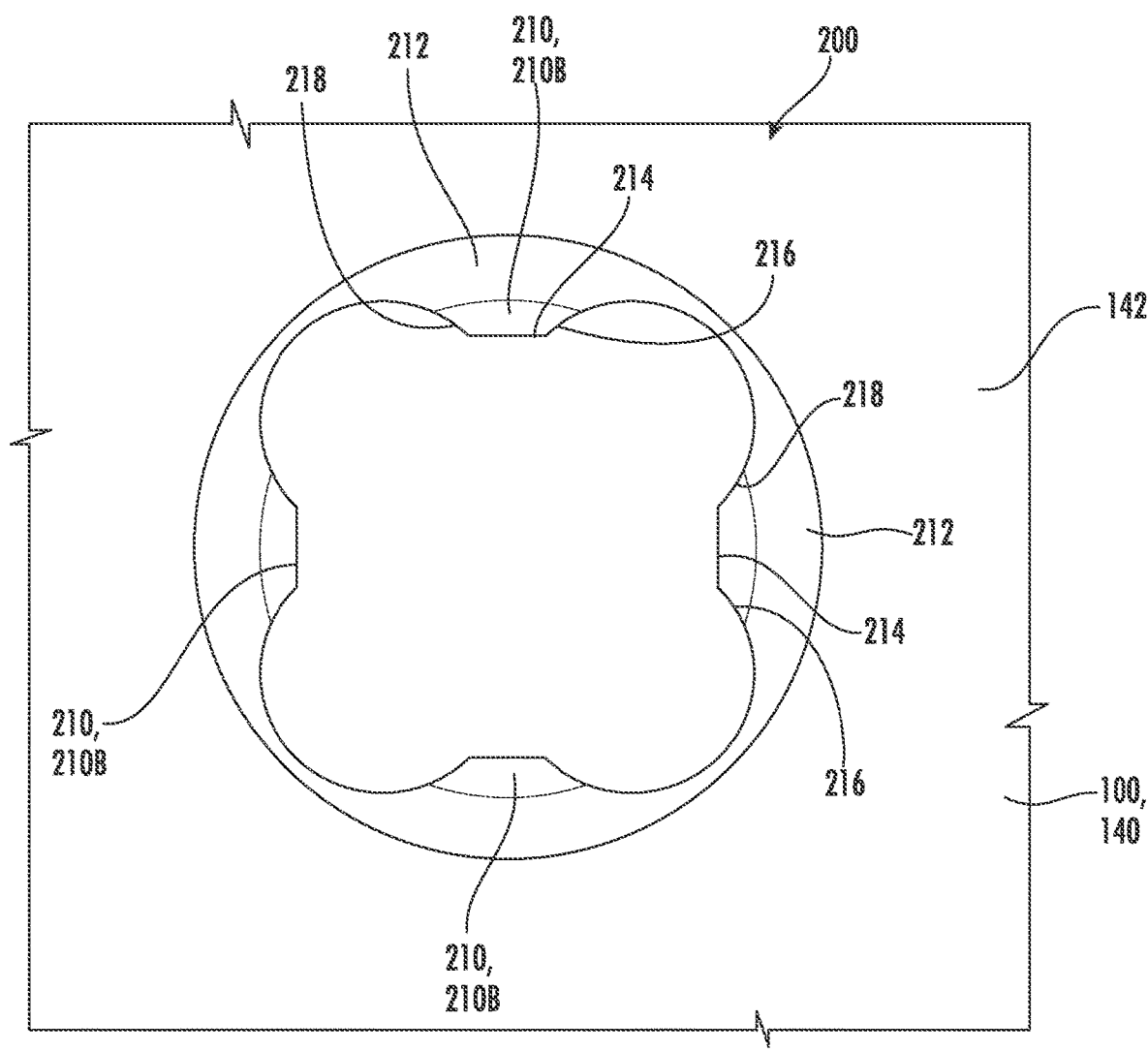
FIG. 8 is a bottom view of the variable angle locking mechanism shown in FIG. 3.

Referring to FIGS. 3-8, in accordance with preferred embodiments of the present disclosure, the finned opening 200 formed in the bone plate 140 includes an inner surface 202 and a plurality of inwardly protruding fins 210 that extend toward a central axis 201 of the finned opening 200. Each fin 210 includes a base 212, a terminal end or tip 214, and side surfaces 216, 218. The bases 212 forming concave portions 220.

In one embodiment, the concave portions 220 are smooth and non-threaded, and as illustrated, the entire inner surface 202 of the finned opening 200 can be devoid of any threads. The bases 212 can extend from the inner surface 202 of the finned opening 200.

As shown, in some embodiments, the fins 210 are integrally connected to, and protruding from, the inner surface 202 of the finned opening 200. The finned opening 200 may include a radius between the inner surface 202 and the top of the fins 210 and each fin 210 may taper in thickness from its base 212 to its terminal end or tip 214. Thus arranged, the finned opening 200 may be seen to have a jagged circumference formed by protruding fins 210. The protruding fins 210 may form a concave portion of the inner surface 202. The protruding fins 210 have bases 212 that meet the inner surface 202 along planes as described in greater detail below.

As shown, in some embodiment, as the fins 210 extend toward the central axis 201 of the finned opening 200, the fins 210 can taper to form inwardly tapered side surfaces 216, 218. Alternatively, the side surfaces 216, 218 of the fins 210 may taper outwardly or may be parallel with each other. The terminal ends or tips 214 can have any shape suitable for engaging the head portion 194 of the fastener 190. For example, the terminal ends or tips 214 can be rounded, pointed, square, rectangular, or any other appropriate configuration. Generally speaking, the fins 210 may be trapezoidally-shaped, rounded, oval, square, rectangular, curved, rhomboid, diamond-shaped, triangular, or the like. The fins 210 may be provided as a series of concavely indented, inwardly protruding fins that are adapted to secure a head 194 of a fastener 190 in place at varying angles (e.g., fins 210 engage the threads or other surfaces formed on the head portion 194 of the fastener 190). Additional information on the configuration and nature of the fins can be found in U.S. Pat. No. 8,105,367, which is incorporated herein by reference in its entirety.

By providing a non-threaded inner surface 202, the fastener 190 can be inserted into the finned opening 200 at a desired insertion angle (e.g., an angle between a longitudinal axis 196 (FIG. 2) of the fastener 190 and the central axis 201 of the finned opening 200). The central axis 201 and the longitudinal axis 196 can be co-linear so that the insertion angle is zero, or the central axis 201 and the longitudinal axis 196 can be non-co-linear with an insertion angle of up to about +/−15 degrees. Varying the insertion angle is possible because there are not any threads in the finned opening 200 to interfere with the desired insertion angle. As will be described in greater detail, in use, the fins 210 are intended to slightly bend or deform in order to secure the fastener 190 in place in the finned opening 200.

As shown in FIGS. 3-8, in one example embodiment, the finned openings 200 include a plurality of first or upper fins 210A and a plurality of second or lower fins 210B. That is, the finned openings 200 may include a first or upper row of fins including a plurality of first or upper fins 210A and a second or lower row of fins including a plurality of second or lower fins 210B, wherein the first or upper row of fins is spaced from the second or lower rows of fins. In use, the first or upper row of fins are positioned closer to a first or upper surface of the implant and the second or lower fins are positioned closer to the opposite or lower surface of the implant. In use, the upper fins 210A and the lower fins 210B are axially spaced from each other so that there is a space therebetween so that a threaded portion or the like of the head portion 194 of the fastener 190 may be positioned within this space.

In one embodiment, as shown, the upper fins 210A may be stacked or aligned with the lower fins 210B. That is, in one embodiment, the upper fins 210A and the lower fins 210B are positioned circumferentially about the finned opening 200 in a vertically stacked position. For example, in one embodiment, the upper and lower rows of fins may each include four fins positioned ninety-degrees apart in a vertically stacked position. That is, in one embodiment, the upper row of fins and the lower row of fins may include four upper fins 210A oriented ninety-degrees apart around the finned opening 200 and four lower fins 210B oriented directly beneath the upper fins 210A. Alternatively, it is envisioned that the upper and lower rows of fins may include more of less fins. For example, the upper and lower rows of fins may each include three fins positioned 120 degrees apart in a vertically stacked position, six fins positioned 60 degrees apart in a vertically stacked position, etc. Moreover, it is envisioned that the upper and lower fins may be positioned offset, or partially offset, from each other. That is, the upper and lower fins may not be positioned in a vertically stacked relationship but rather the upper fins may be positioned offset, or partially offset, from the lower fins (e.g., the upper fins may be positioned in-between the lower fins). In an alternate embodiment, it is envisioned that the upper row of fins and the lower row of fins may include different number of fins such as, for example, the upper row may include four fins and the lower row of fins may include five fins, or the like.

In addition, and/or alternatively, as will be described in greater detail below, one or more of the individual fins 210 residing within the upper and lower rows of fins may have different properties, configurations, etc. (used interchangeably herein without the intent to limit) from one or more of the other fins residing within the upper and lower rows of fins. That is, at least one of the fins 210 has a different configuration from at least one of the other remaining fins. As shown, in one embodiment, the different configuration may correspond to a different length or relative inscribed diameter (used interchangeably) (e.g., measured from a base 212 of the fin 210 to a terminal end 214 of the fin 210), or a different thickness (e.g., a different cross-sectional diameter, thickness, etc.), or a combination thereof. Thus arranged, at least one of the fins may be said to have a first configuration and at least one of the fins may be said to have a second configuration. Generally speaking, the second configuration is smaller, less material fins that will enhance/improve the construct. For example, in one embodiment, the first configuration may have a thickness at the terminal end 214 of the fin 210 of approximately 0.009 inches. The second configuration may have a thickness at the terminal end 214 of the fin 210 of approximately 0.009 inches or less, although as will be appreciated by one of ordinary skill in the art these dimensions are just one example and the fins may have other dimensions. Moreover, in one embodiment, the second configuration may have a larger inscribed diameter as compared to the first configuration.

As shown, in one embodiment, each of the upper fins 210A and the lower fins 210B in the first and second rows may be arranged and configured in a vertically stacked relationship so that the lower fins 210B are aligned with, positioned beneath, etc. the upper fins 210A in a vertical stack. In one embodiment, for each of the vertical stacks of upper and lower fins 210A, 210B, the upper fin 210A may have a different configuration as compared to the lower fin 210B in its vertical stack (e.g., positioned directly above it). That is, for example, the upper fin 210A in a vertical stack may have a first configuration and the lower fin 210B in the vertical stack may have the second configuration.

That is, for example, in one embodiment, the upper and lower fins 210A, 210B may extend into the opening toward the central axis 201 of the finned opening 200 by a different amount, extent, or the like. In addition, the shorter fins may have a different cross-sectional area (e.g., a different thickness) relative to the longer fins. Thus arranged, during insertion of a fastener 190 into a finned opening 200, the threads formed on the head portion 194 of the fastener 190 will start to engage the longer fins 210 first thus providing initial fixation. Subsequently, the head portion 194 of the fastener 190 will engage the shorter fins thereby providing increased fixation strength.

In addition, and/or alternatively, each of the upper fins 210A and the lower fins 210B may alternate configurations as the fins 210 are circumferentially disposed in the finned opening 200. For example, as shown, with the finned opening 200 including four upper fins 210A and four lower fins 210B, although the number of fins may be varied, orientated in a vertically stacked relationship so that, for example, the upper and the lower fins may be said to reside at positions A, B, C and D, respectively, corresponding to, for example, 12 O'clock, 3 O'clock, 6 O'clock, and 9 O'clock, the upper fin 210A at position A (e.g., 12 O'clock) and position C (e.g., 6 O'clock) may have a different configuration as compared to the lower fin 210B at position A (e.g., 12 O'clock) and position C (e.g., 6 O'clock) (e.g., the upper fins 210A may have a first configuration and the lower fins 210B may have a second configuration). Similarly, the upper fins 210A located at position B (e.g., 3 O'clock) and position D (e.g., 9 O'clock) may have a different configuration as compared to the lower fins at position B (e.g., 3 O'clock) and position D (e.g., 9 O'clock) (e.g., the upper fins 210A may have the second configuration and the lower fins 210B may have the first configuration). Thus arranged, as one moves about the circumference of the finned opening 200, the upper fin 210A at each clock position may have a different configuration from the lower fin 210B at the same clock position, with the upper and lower fins 210A, 210B alternating configurations as one traverses about the circumference of the finned opening 200. That is, as one moves about the circumference of the finned opening 200, the first fin at a first clock position may have a different length and/or different cross-section than the second fin at the first clock position. Thereafter, at a subsequent clock position, the second fin at a second clock position may have a different length and/or different cross-section than the first fin at the second clock position, and so on as one traverses about the circumference of the finned opening 200. For example, in one embodiment, the first fin at a first clock position may have a longer length than the second fin at the first clock position. In addition, and/or alternatively, the first fin at the first clock position may have a smaller cross-sectional area (e.g., reduced thickness) than the second fin at the first clock position. Thereafter, at a subsequent clock position, the second fin at a second clock position may have a longer length than the first fin at the second clock position. In addition, and/or alternatively, the second fin at the second clock position may have a smaller cross-sectional area (e.g., reduced thickness) than the first fin at the second clock position, and so on as one traverses about the circumference of the finned opening 200.

In use, as will be appreciated by one of ordinary skill in the art, insertion of a fastener 190 into a finned opening 200 results in the upper and lower fins 210A, 210B being threaded into the head portion 194 of the fastener 190. Thus arranged, in use, the fins 210 act to prevent backing out of the fastener 190 from the implant 100. In use, the fastener 190 may be inserted into the finned opening 200 at a variety of angles, while still securing the fastener 190 to the implant 100.

As will be appreciated by one of ordinary skill in the art, the dimensions of each individual fin 210 is typically dependent at least in part upon the pitch and threads on the head portion 194 of the fastener 190. For example, a larger plate/implant 100 for use with a larger fastener 190 (for example, for use on a femur bone) will likely be thicker and will have larger and thicker fins than a smaller plate/implant 100 (for example, for use on a smaller bone). In specific implementations, the fins 210 are particularly thin so that they can be moved up or down and deform under pressure. That is, upon insertion of a fastener 190 into a finned opening 200, the upper and lower fins 210A, 210B will either deform, deflect, or combinations thereof. Thus arranged, in some embodiments, the fins 210 may be pressed toward the edges of the finned opening 200. A non-limiting exemplary range of thicknesses for the fins 210 is from about 0.1 mm to about 5 mm, although larger and smaller sizes are possible. In use, the fins 210 are intended to fit between threads or the like formed on the head portion 194 of the fastener 190. In one embodiment, a ratio of a thread pitch formed on the head portion 194 of the fastener 190 to the distance or spacing between the upper and lower fins 210A, 210B is between 0.85 to 1.15.

In some embodiments, the finned openings 200 may include a countersink. In use, as will be appreciated by one of ordinary skill in the art, by providing a countersink, the head portion 194 of the fastener 190 may interact with the countersink to facilitate improved polyaxial rotation of the fastener 190 relative to the implant 100.

In some embodiments, the bases 212 of the upper fins 210A all meet, for example, in substantially the same plane and then angle downwardly and inwardly at a similar angle or slope. Similarly, the bases 212 of the lower fins 210B all meet, for example, in substantially the same plane and then angle downwardly and inwardly at a similar angle or slope. The downward angle of the upper and lower fins 210A, 210B may be the same, although it is envisioned that the upper fins 210A may be angled at a different angle than the lower fins 210B. In some embodiments, one or both of the upper and lower planes may be parallel to a surface of the implant. Alternatively, one or both of the upper and lower planes may be non-parallel to a surface of the implant.

In some embodiments, the central axis 201 of the finned openings 200 may be perpendicular to the surface of the implant or the central axis 201 may be non-perpendicular to the implant.

As will be appreciated, the finned openings 200 provide an improved stable connection between the fasteners 190 and the implant 100 that permits different angles to be obtained between the fasteners 190 and the implant 100, while securing the fastener 190 to the implant 100. This allows the surgeon greater versatility to reach denser areas of bone or capture random bone fragments that are in irregular positions, for example, in cases of severe fractures with highly fragmented bones. The fastener and implant system advantageously allows the surgeon to choose the angle at which the fastener 190 is inserted through, and rigidly affixed in, an opening of the implant 100.

In use, the plurality of fins 210 may engage the head portion 194 of the fastener 190 when the fastener 190 is inserted into the finned opening 200 such that the fastener 190 can be inserted and retained at any one of a plurality of angles relative to the finned opening 200 (e.g., the configuration of the fins act to improve the resistance to cantilever load on the fastener 190 when locked into the fins regardless of the direction or angle of screw relative to the implant 100). The fins 210 may deflect and/or deform so that the fins 210 are interposed between the threads or the like on the head 194 of the fastener 190. Thus arranged, the fins 210 grasp, for example, the threads formed on the head 194 of the fastener 190 in order to secure the fastener 190 in place relative to the implant 100 at any desired insertion angle. As previously mentioned, the fins 210 can be very thin so that as the threads start to grab the fins 210, the fins 210 can move up or down as appropriate to engage the threads and secure the fastener 190 in the finned opening 200. The threads engage the fins 210 so that the fins 210 fit between the threads. The movement of fins 210 can be a permanent deformation, so that the fins 210 cannot flex back and allow the fastener 190 to work its way out.

The foregoing description has broad application. Accordingly, the discussion of any embodiment is meant only to be explanatory and is not intended to suggest that the scope of the disclosure, including the claims, is limited to these example embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The term "a" or "an" entity, as used herein, refers to one or more of that entity. As such, the terms "a" (or "an"), "one or more" and "at least one" can be used interchangeably herein. The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein. The phrases "at least one", "one or more", and "and/or", as used herein, are open-ended expressions that are both conjunctive and disjunctive in operation.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another. The drawings are for purposes of illustration only and the dimensions, positions, order and relative sizes reflected in the drawings attached hereto may vary.

What is claimed is:

1. An orthopedic implant comprising:
   a bone contacting surface;
   an upper surface opposite the bone contacting surface; and
   a plurality of openings extending between the bone contacting surface and the upper surface, each of the plurality of openings being arranged and configured to receive a fastener for coupling the orthopedic implant to a patient's bone in use;
   wherein:
   at least one of the plurality of openings including first and second rows of fins;

each of the first and second rows of fins including a plurality of fins circumferentially disposed about the at least one opening, the plurality of fins being arranged and configured to engage a head portion of a respective fastener inserted therein; and each of the plurality of fins in the first and second rows of fins has a first configuration or a second configuration, the second configuration being different than the first configuration;

wherein:

each of the plurality of fins in the first row of fins is arranged and configured in a vertically stacked relationship with one of the plurality of fins in the second row of fins so that the second row of fins is circumferentially aligned with the first row of fins;

for each of the vertical stacks of first and second rows of fins, the fin in the first row of fins includes one of the first configuration and the second configuration and the fin in the second row of fins in its respective vertical stack includes the other one of the first configuration and the second configuration; and each fin in the first and second rows of fins includes an alternating configuration of fins between the first and second configurations as the fins are circumferentially disposed in the at least one opening.

2. The orthopedic implant of claim 1, wherein each of the first and second rows of fins include four fins orientated ninety-degrees apart so that the four fins in the first and second rows of fins are positioned in circumferential positions A, B, C, and D;

wherein:

the fin in the first row of fins at positions A and C includes the first configuration;

the fin in the first row of fins at positions B and D includes the second configuration;

the fin in the second row of fins at positions A and C includes the second configuration; and the fin in the second row of fins at positions B and D includes the first configuration.

3. The orthopedic implant of claim 1, wherein the first and second configurations of fins is selected from one of a different length, a different thickness, or a combination thereof.

4. The orthopedic implant of claim 1, wherein at least one of the fins in the first row of fins extends into the at least one opening farther than the fin in the second row of fins in the vertically stacked relationship.

5. An orthopedic implant comprising:

a bone contacting surface;

an upper surface opposite the bone contacting surface; and a plurality of openings extending between the bone contacting surface and the upper surface, each of the plurality of openings being arranged and configured to receive a fastener for coupling the orthopedic implant to a patient's bone in use;

wherein:

at least one of the plurality of openings include first and second rows of fins;

each of the first and second rows of fins including a plurality of fins circumferentially disposed about the at least one opening, the plurality of fins being arranged and configured to engage a head portion of a respective fastener inserted therein;

each of the plurality of fins in the first row of fins is arranged and configured in a vertically stacked relationship with one of the plurality of fins in the second row of fins so that the second row of fins is circumferentially aligned with the first row of fins; and at least one of the plurality of fins in the first and second rows of fins has a first configuration and at least one of the plurality of fins in the first and second rows of fins has a second configuration, the second configuration being different than the first configuration;

wherein at least one of the fins in the first row of fins extends into the at least one opening farther than the fin in the second row of fins in the vertically stacked relationship; and wherein at least one of the fins in the first row of fins has a thinner cross-sectional area at a tip thereof as compared to the fin in the second row of fins in the vertically stacked relationship.

6. The orthopedic implant of claim 1, wherein the orthopedic implant is a bone plate.

7. A bone plate comprising:

a top surface;

a bone contacting surface; and at least one opening extending between the top surface and the bone contacting surface, the at least one opening including first and second rows of fins, each of the first and second rows of fins including a plurality of fins circumferentially disposed about the at least one opening, the fins in the first row of fins being aligned in a vertically stacked relationship with the fins in the second row of fins;

wherein, for each vertically stacked relationship, the fin in the first row of fins has one of a first configuration and a second configuration, the fin in the second row of fins has the other one of the first configuration and the second configuration, the first configuration being different than the second configuration, wherein the first configuration is a different length as measured from a base of the fin to a tip of the fin, the second configuration is a thinner cross-sectional area at the tip of the fin.

8. A bone plate comprising:

a top surface;

a bone contacting surface; and at least one opening extending between the top surface and the bone contacting surface, the at least one opening including first and second rows of fins, each of the first and second rows of fins including a plurality of fins circumferentially disposed about the at least one opening, the fins in the first row of fins being aligned in a vertically stacked relationship with the fins in the second row of fins;

wherein, for each vertically stacked relationship, the fin in the first row of fins has one of a first configuration and a second configuration, the fin in the second row of fins has the other one of the first configuration and the second configuration, the first configuration being different than the second configuration, wherein the fins in the first row of fins alternate first and second configurations as one moves about a circumference of the at least one opening; and the fins in the second row of fins alternate first and second configurations as one moves about the circumference of the at least one opening.

9. The bone plate of claim 8, wherein the first configuration is a different length as measured from a base of the fin to a tip of the fin, the fins in the first and second row of fins alternating first and second configurations as one moves about a circumference of the at least one opening so that a longer length fin alternates between the first and second rows of fins as one moves about the circumference of the at least one opening.

10. A bone plate comprising:
- a top surface;
- a bone contacting surface; and
- at least one opening extending between the top surface and the bone contacting surface, the at least one opening including first and second rows of fins, each of the first and second rows of fins including a plurality of fins circumferentially disposed about the at least one opening, the fins in the first row of fins being aligned in a vertically stacked relationship with the fins in the second row of fins;
- wherein, for each vertically stacked relationship, the fin in the first row of fins has one of a first configuration and a second configuration, the fin in the second row of fins has the other one of the first configuration and the second configuration, the first configuration being different than the second configuration,
- wherein each of the first and second rows of fins include four fins orientated ninety-degrees apart so that the four fins in the first and second rows of fins are positioned in circumferential positions A, B, C, and D;
- wherein:
  - the fin in the first row of fins at positions A and C includes the first configuration;
  - the fin in the first row of fins at positions B and D includes the second configuration;
  - the fin in the second row of fins at positions A and C includes the second configuration; and
  - the fin in the second row of fins at positions B and D includes the first configuration.

* * * * *